United States Patent [19]

Quenin et al.

[11] Patent Number: 5,042,978
[45] Date of Patent: Aug. 27, 1991

[54] CONTAINER USING A MASS OF POROUS MATERIAL FOR LIQUID RETENTION

[75] Inventors: John A. Quenin, Rochester; Raymond F. Jakubowicz, Rush; Richard L. Columbus, Rochester, all of N.Y.

[73] Assignee: Eastman Kodak Company, Rochester, N.Y.

[21] Appl. No.: 472,454

[22] Filed: Jan. 29, 1990

Related U.S. Application Data

[63] Continuation-in-part of Ser. No. 391,225, Aug. 8, 1989, abandoned.

[51] Int. Cl.$^5$ .......................... A61M 1/00; A61B 5/00
[52] U.S. Cl. .................... 604/317; 604/319; 128/760
[58] Field of Search ................ 604/317, 319; 128/760, 128/761

[56] References Cited

U.S. PATENT DOCUMENTS

| | | | |
|---|---|---|---|
| 3,126,874 | 3/1964 | Exner | 120/44 |
| 3,441,950 | 4/1969 | Miller | 346/140 |
| 3,967,286 | 6/1976 | Andersson et al. | 346/140 |
| 4,017,871 | 4/1977 | Hubbard | 346/140 |
| 4,095,237 | 6/1978 | Amberntsson et al. | 346/140 |
| 4,306,245 | 12/1981 | Kasugayama et al. | 346/140 |
| 4,377,815 | 3/1983 | Henning et al. | 346/140 |
| 4,436,439 | 3/1984 | Koto | 400/126 |
| 4,630,758 | 12/1986 | Mutoh | 222/189 |
| 4,771,295 | 9/1988 | Baker et al. | 346/1.1 |
| 4,794,409 | 12/1988 | Cowger et al. | 346/140 |

OTHER PUBLICATIONS

*NASA Tech Briefs*, p. 88, Apr., 1988, "Surface Tension Confines Cryogenic Liquid".

*Primary Examiner*—Ronald Frinks
*Assistant Examiner*—Robert H. Clarke
*Attorney, Agent, or Firm*—Dana M. Schmidt

[57] ABSTRACT

There are disclosed a container and a method of aspirating body liquids, that allow controlled capillary attraction to hold the liquid in place for storage, but not so tightly that the liquid cannot be aspirated away. A mass of compatible porous material is used in the container and comprises fibers with a controlled capillary attraction that supports a column of water that is between about 2 mm and about 60 mm in height.

9 Claims, 4 Drawing Sheets

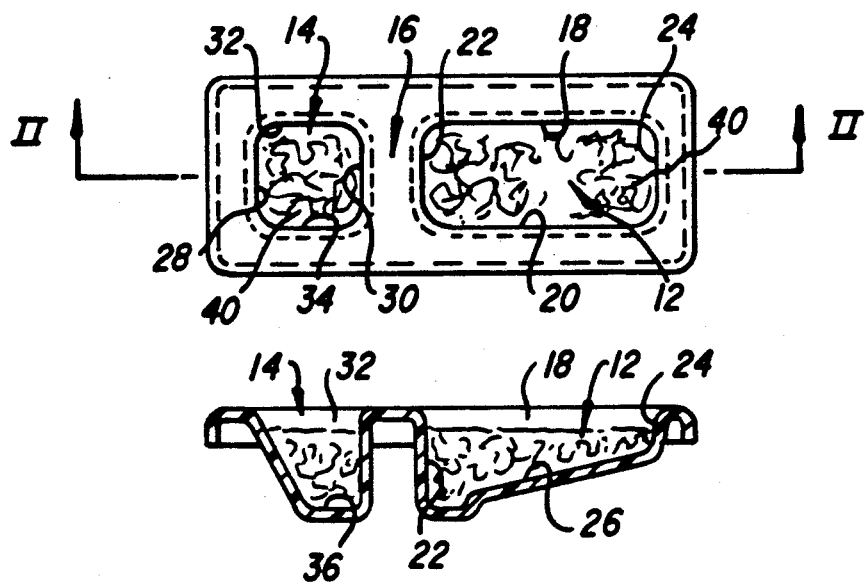
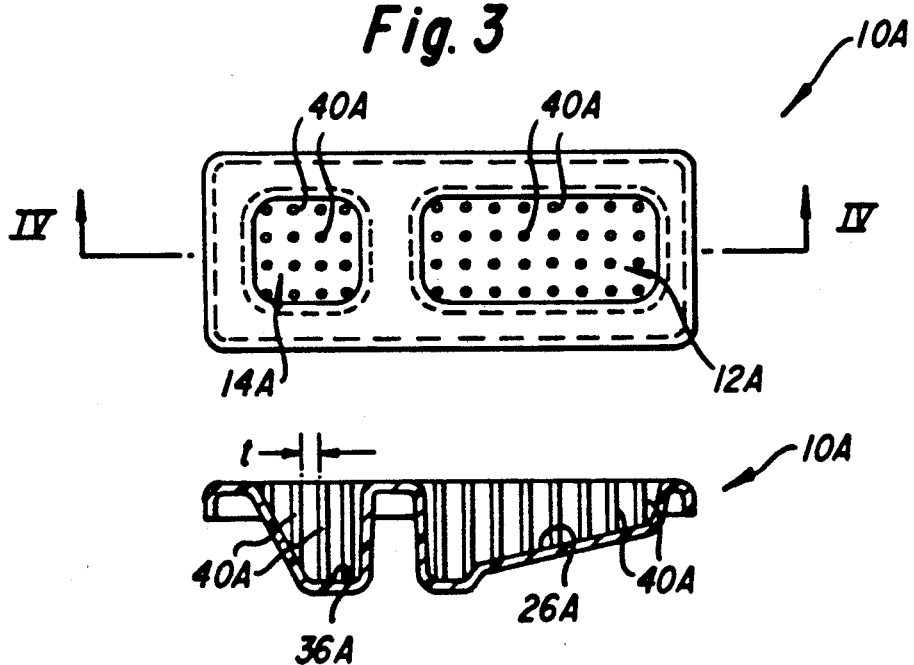

CONTAINER USING A MASS OF POROUS MATERIAL FOR LIQUID RETENTION

This is a continuation-in-part of application Ser. No. 391,225, filed Aug. 8, 1989, now abandoned.

FIELD OF THE INVENTION

The invention relates to a container for holding liquid, particularly body liquids, in a zero or micro-gravity environment.

BACKGROUND OF THE INVENTION

Nothing points to the difference between partial or zero gravity fields, and earth-normal (1 g) gravity, more than the question of liquid handling. On Earth, if a clinician wishes to sample a body liquid, such as blood serum, to analyze its analytes, such a person can pour the sample into an open cup and simply aspirate what is needed from the cup. In a space station, however, operating with less than or a total absence of, normal gravity, this will not work. First of all, liquid cannot be "poured". Even assuming it somehow finds its way into an open container, there is no reason for it to stay there. Any inertial effect on the container is likely to eject one or more globs of the liquid, to interfere with or contaminate the environment in which the analyzer exists. The logical "solution" to such a problem is to place a cap or cover over the cup or container, to retain the liquid. The difficulty with that is the open volume of the container under the cap will simply invite the liquid to disperse itself throughout the total container volume, leaving air bubbles in between the dispersed globs. Any attempt then to aspirate liquid from the container by inserting an aspirator through the cap, is likely to end up with the aspirator encountering air rather than liquid, or a combination of air and liquid.

Therefore, there has been a need, prior to this invention, for a container for body liquids to be used in combination with an aspirator, that will avoid the above-noted problems.

Liquid absorbing masses have been used in other containers, such as porous baffles to reduce slosh during operation and to prevent rapid release of fuel from a ruptured fuel tank of a racing car. However, these have not been associated with aspirators of body liquids, nor has there been any suggestion as to how they should be modified to allow them to be used with such aspirators in weightless environments.

SUMMARY OF THE INVENTION

We have constructed a container and a method of aspirating that solves the above-noted problems created by weightlessness.

More specifically, there is provided, in accord with one aspect of the invention, a combination of a liquid aspirator and a container for body liquids, the container comprising a mass of compatible porous material that will absorb the body liquid of choice, and means for holding the mass of material, and any liquid contained therein in a predetermined location, the mass of material comprising (a) fibers having a capillary attraction which will support a column of water that is between about 2 mm and about 60 mm in height, or (b) an open-cell foam having liquid attraction and liquid retention that is equivalent to that of said fibers.

In accord with another aspect of the invention, there is provided a method of aspirating body liquids in an environment of reduced gravity, comprising injecting the liquid into a site portion of a mass of wettable, liquid-compatible porous material that will absorb the body liquid, the mass of material comprising fibers having a capillary attraction which will support a column of water that is between about 2 mm and about 60 mm in height; inserting the open end of an aspirator into the mass of porous material at the site portion in which the liquid resides; and creating a sufficient partial vacuum in the aspirator to draw at least some of the liquid out of the mass of material.

Therefore, it is an advantageous feature of the invention that body liquids can be stored in zero or micro-gravity conditions, and readily aspirated out without air entrainment, using conventional aspirators.

It is a related advantageous feature of the invention that storage apparatus and an aspiration method are provided that minimize the risk of body liquids floating out of a container to contaminate the environment.

Other advantageous features will become apparent upon reference to the detailed description of the preferred embodiments, when read in light of the attached drawings.

BRIEF DESCRIPTION OF THE DRAWINGS

FIG. 1 is a plan view of a container constructed in accordance with the invention;

FIG. 2 is a section view taken generally along line II—II of FIG. 1;

FIG. 3 is a plan view similar to that of FIG. 1, but illustrating an alternate embodiment;

FIG. 4 is a section view taken generally along the line IV—IV of FIG. 3;

DESCRIPTION OF THE PREFERRED EMBODIMENTS

Figure 5:
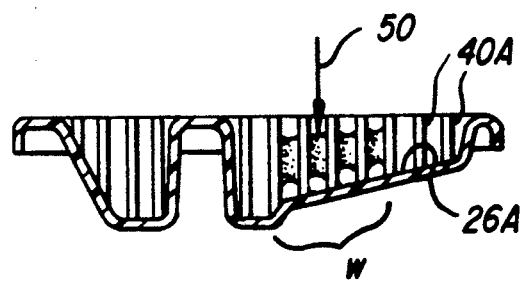
FIG. 5 is the section view of FIG. 4, showing a body liquid, such as serum, in place in the container.

The invention is hereinafter described with respect to preferred embodiments wherein blood serum and a reference fluid are stored and aspirated out in a zero gravity environment. In addition, it is useful for any stored body liquid, regardless of the particular aspirator construction used to remove liquid from the container, and regardless of the amount of gravity that may be present.

Directions such as "up" or "bottom" are used as referents in an environment where there is gravity. In a space station without gravity, such directions are arbitrary.

Thus, the apparatus of the invention comprises a liquid storage container and an aspirator. What is important about the container is not any sidewalls that might be present as an aid in holding in place the mass of material hereinafter described, but rather that mass of material itself. Thus, "container" is used broadly to mean the means for holding that mass, as well as the mass itself.

The mass of porous material needs to be liquid-absorbing for the body liquid of choice, with capillary attraction sufficient to create an intermediate level of capillary force. Regarding the liquid absorption, materials that repel the body liquid, e.g., repel blood serum, are generally unsatisfactory in defining the liquid storage area unless the repulsion can be overcome by a coating that renders the material more absorbent. The choice of materials which will be satisfactory will vary, depending on the body liquid to be absorbed.

Notwithstanding the above, surfaces on the periphery of the container can be repellant to force the liquid to occupy a center region where the material is rendered liquid absorbent. This repellency in effect creates a confining "wall".

The following fibrous materials have been found to be useful for their tendency to absorb blood serum and to be wetted in their mass, when tested individually: uncoated glass fibers; nylon fiber obtainable under the trade name "Scotchbrite 96" from 3M (apparently uncoated); polyester fiber, such as quilt liner fiber manufactured by Carlee Corp. and coated with acrylic emulsion obtainable under the trademark "Rhoplex TR-407" from the manufacturer Rohm and Haas; or polyester fiber such as that used in air filters obtained under the tradename Part 2-520 from the manufacturer R. P. Fedder and coated with polyvinyl chloride; uncoated cotton fibers; and uncoated cellulose acetate fibers obtainable as bulk filter tow from Eastman Kodak Company. Mixtures of fibers are also believed to be useful.

The following materials have been found to give unacceptable wettability and absorptions of blood serum when used massed: steel wool.

Regarding acceptable level of capillary attraction, if the capillary attraction is reduced to the point that the body liquid does not remain absorbed by the mass, the container fails. In an analyzer used in zero-level or micro-level gravity, this is insufficient as the liquid can escape from the mass and become free-floating globs, leading to contamination. If the capillary attraction is so strong that the mass does not readily give up the liquid to the aspirator, this in turn creates an air bubble in the tip of the aspirator, representing the amount of resistive residual vacuum that the mass produced in its tight capillary attraction. In some systems, a small air bubble is acceptable, but in most systems, the air bubble volume is mistaken as liquid volume and results in an incorrect volume of liquid ultimately being dispensed. Methods of detecting, measuring, and compensating for this air volume are being developed, but they add cost and are not considered desirable.

Generally, the preferred form of the porous material is a fibrous one, and whether the wettability and capillary attraction of a fibrous material is satisfactory for use, is readily determined by the height of a water column that the material will support. That is, the fibers of choice are inserted, with the same desired density or compactness as will be used in the container, into a body of water, and the height to which the water rises is a measure both of the fibrous material's wettability and intermediate amount of capillary attraction. To the extent the fibers have a particular orientation, the mass is introduced into the water with the fibers extending generally vertically.

As the Table listed hereafter illustrates, such column height is preferably between about 2 mm and about 60 mm. Less than 2 mm provides insufficient attraction and the liquid is likely to escape from the container, particularly in a micro-gravity environment. Comparative Example No. 1 indicates that a very strong capillary attraction producing a long water column correlates with poor aspirability by a pipette. It is believed that the actual upper limit is about 60 mm, in light of the decreased performance (only "fair") of cotton at 51 mm.

TABLE

| EX. | MATERIAL | WETTABILITY | ASPIRABILITY | COATING USED | FIBER DIA. (mm) | WATER COLUMN HGT. (mm., approx.) |
|---|---|---|---|---|---|---|
| 1 | Glass Fiber | Excellent | Fair | None | 0.003 (approx.) | 13 |
| 2 | Nylon Fiber | Good | Good | Unknown* | 0.08 | 3.8 |
| 3 | Polyester Fiber | Excellent | Excellent | Acrylic** | 0.01 | 5.1 |
| 4 | Polyester Fiber | Excellent | Excellent | PVC | 0.01 | 3.6 |
| 5 | Cotton | Excellent | Fair | None | 0.003 (approx.) | 51 |
| 6 | Cellulose Acetate (filter tow, bulked) | Excellent | Good | None | 0.003 (approx.) | 9 |
| 7 | Integral Plastic Fingers (FIG. 5) | Good | Excellent | None | 0.8 | 2.2 |
| Comp. Ex. 1 | Cellulose Acetate (cigarette filter) | Excellent | Poor | None | 0.003 (approx.) | >180 |
| Comp. Ex. 2 | Steel Wool | Poor | (Not Tested) | None | 0.03 | .3 |

*Contains unknown binders applied by manufacturer.
**Rohm and Haas Rhoplex aqueous acrylic, TR-407 emulsion, applied by manufacturer.

Still other materials have to be ruled out as unacceptable, as they influence test results to be conducted on the liquid. In the case of blood serum, this precludes the use of common surfactants to modify wettability of the porous material. Such surfactants generally include a salt or detergent, either of which will grossly affect some tests.

In addition, it has been found that certain open-cell foams are equivalent to the above-noted fibers because they provide similar properties of intermediate amounts of capillary attraction which however do not interfere with aspiration of the liquid out of the foam by an aspirator. For reasons that are not clear, the useful foams do not however provide the same support of a column of water. Instead, the number of pores per lineal cm and the % porosity appear to be a more useful measure of acceptability for a foam. Judging from these properties that exist in the urethane and melamine foams that have been found to work, it is estimated that the pore distribution should be, depending on the material, from about 2 to about 40 pores/cm, with a % porosity that is about 97%. As in the case of the fibers described above, the foam should provide acceptable wettability.

Particularly useful foams include the following:

1) Polyurethane foam, both uncoated and polyester coated Optimum pore size is about 4 pores per cm., which is the largest pore size commercially available. The next smaller pore size available is 11.8 pores per cm, which has been found to be a little too small. Based on this information, an acceptable pore size range is 2 to 8 pores per cm. Void volume of all samples, regardless of pore size, is 97%.

2) Melamine foam

There is only one pore size commercially available. By visually comparing the melamine to other samples with known pore size, it is estimated that there are about 39 pores per cm. Based on manufacturer's data and a comparison to the behavior of the polyurethane foam, it is estimated that th useful range of melamine foam is about 12 to about 40 pores/cm.

The following Table II lists details about the foams. "Comp. Ex." are comparative examples:

TABLE II

| Ex. | Material | Wettability | Aspirability | Coating Used | Pore Distribution | Water Column Ht. (mm) |
| --- | --- | --- | --- | --- | --- | --- |
| 8 | polyurethane foam @ | good | good | none | 3.9/cm | 0.3$ |
| 9 | polyurethane foam @ | good | good | polyester @ @ | 3.9/cm | 0.3$ |
| 10 | melamine foam $$ | excellent | good | none | 3.9/cm | 6.4 |
| Comp. Ex. 3 | polyurethane foam | poor | good | none | 11.8/cm | 0.3$ |
| Comp. Ex. 4 | natural sponge | poor | good | none | much larger than 4/cm | 0.3$ |

$Of doubtful accuracy as this is barely above a zero reading.
@As supplied by Rogers under the Tradename RFI-261-10.
@@An aqueous polyester supplied by Eastman Kodak Company under the tradename AQ55D.
$$As supplied by Illbruck under the tradename Willtec.

With regard to Comp. Ex. 4, it has been found that the poor wettability can be cured by coating the sponge with a surfactant such as that available from Olin Manu. under the tradename 10G. However, that also is unsatisfactory because the surfactant acts as a contaminant of the blood serum—that is, it is an interferant in many of the assays that need to be run on the serum sample.

FIG. 1 illustrates a useful container 10, having two storage compartments 12 and 14, divided by an intermediate wall 16. Wall surfaces 18, 20 and 22, 24 provide the opposing side surfaces for the larger compartment 12. The bottom surface is wall surface 26, FIG. 2. Similarly, wall surfaces 28, 30 and 32, 34, FIG. 1, are opposing side surfaces for compartment 14, with a bottom surface 36, FIG. 2.

Between the wall surfaces in each compartment is the requisite mass of compatible porous material 40 described above, which mass is shown as fibers. Any suitable means, not shown, such as water-insoluble adhesive, can be used to retain the fibers or foam between the wall surfaces.

Preferably, the larger compartment 12 is used to retain patient blood serum, while the smaller compartment 14 retains a reference liquid, such as is used in making potentiometric measurements on an ISE test element. Alternatively, the usage of these compartments can be reversed, and in fact, only one compartment can be present.

It is not essential that the mass of porous material be fibers that are manufactured separately from the wall surfaces of the container. As shown in FIGS. 3-7, the mass of fibrous material can be a plurality of flexible columns or fingers projecting integrally away from one of the wall surfaces of the container. Since the container wall surfaces are preferably a plastic that is compatible with body liquids, such as polypropylene, the compatibility requirement is readily met. Parts similar to those previously described bear the same reference numeral, to which the distinguishing suffix "A" is appended. Thus, container 10A has wall surfaces, especially bottom surfaces 26A and 36A, forming two compartments 12A and 14A, as before. However, the mass of porous material 40A in each instance comprises flexible fingers or columns projecting upward from the respective bottom surface. Such "columns" are arranged in rows and columns with preferably uniform spacing "t" between, FIG. 4. The spacing "t" and diameter of the columns is such as to create the desired column of water as shown in the Table. For example, the column diameters can be about 0.08 cm. and "t" can be about 0.25 cm.

When a body liquid is introduced into either compartment 12A or 14A, via arrow 50, FIG. 5 (and a suitable pipette or dispenser, not shown), the liquid is attracted via capillary attraction and surface wettability to the spaces between the columns. It may or may not wet any sidewall, or bottom wall such as wall 26A. The width of this site portion is shown as "w", and is readily visible to an operator, for most body fluids.

Figure 6:
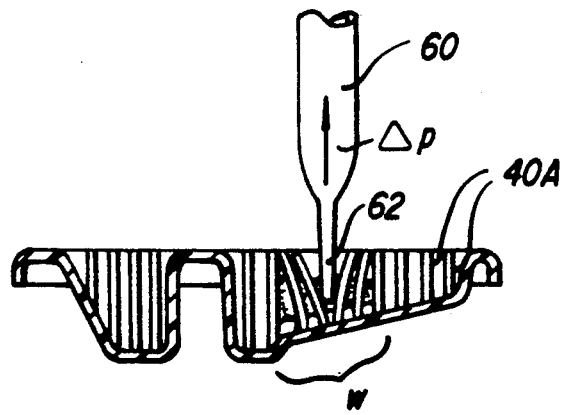
FIG. 6 is the section view of FIG. 5, showing, however, an aspirator in position to aspirate liquid out of the container.

FIG. 6 illustrates why columns or fingers 40A are preferably flexible. To retrieve part of the liquid, a pipette or other type aspirator 60 is inserted between those fingers, at any angle, bending them as shown, until tip 62 of the pipette is within the site portion occupied by the liquid. A partial vacuum ΔP is then formed in the aspirator and the desired amount of liquid is withdrawn.

Figure 7:
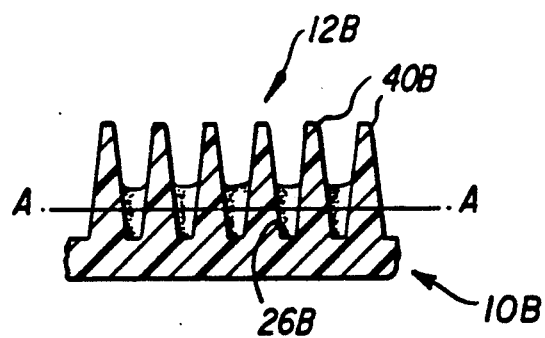
FIG. 7 is a fragmentary, enlarged section view of a portion of a container, similar to a portion shown in FIG. 4, except that it illustrates another embodiment.

Most preferably, the diameter of the fingers is not the constant diameter shown in FIGS. 3-6, but a variable one that produces a cone shape, FIG. 7. Parts similar to those previously described bear the same reference numeral, to which the distinguishing suffix "B" is appended.

Thus, container 10B has a compartment 12B wherein a bottom wall surface 26B has fingers 40B projecting away as in the previous embodiment. However, fingers 40B are shown as extending perpendicular from surface 26B, and most importantly, are cone-shaped. The result is that the dimension between fingers varies (increases) as the distance from wall surface 26B increases. This in turn produces a variable capillary attraction which is greatest at surface 26B, meaning that the liquid will be pulled down to that surface, thus insuring that the meniscus is located a known distance away from surface 26B. As a result, the aspirator need only be inserted so the tip intersects plane A—A, FIG. 7, and the operator can be sure that the aspirator will withdraw liquid, and not air. Another advantage of the variable capillary attraction is that there will be less capillary force at the outer portions of the container, and thus less resistance to the aspiration.

Figure 8:
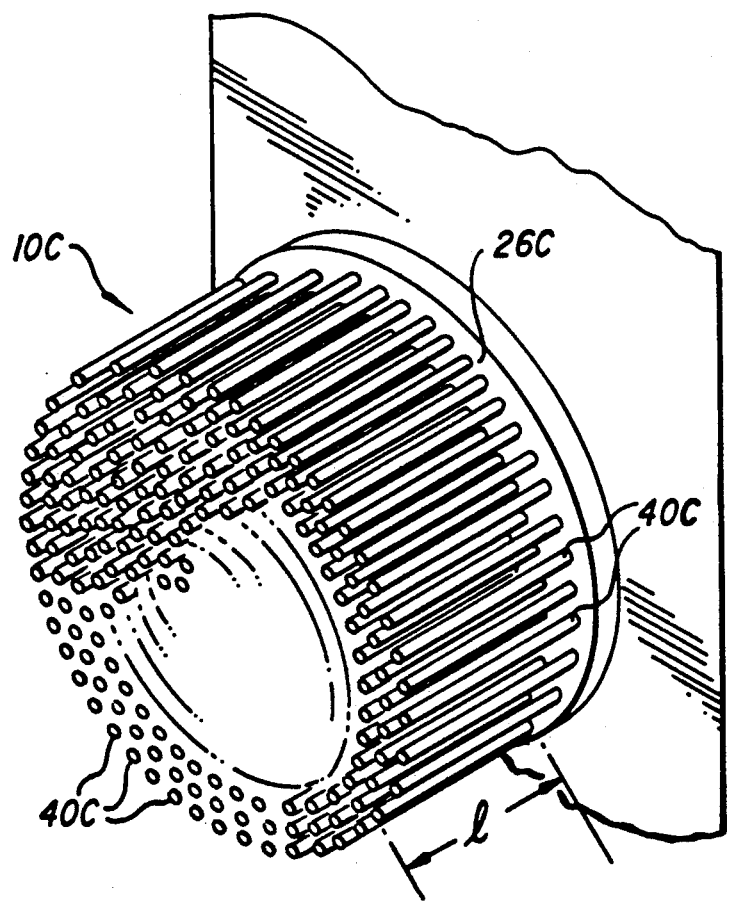
FIGS. 8 and 9 are perspective views of still two other embodiments.

As shown in FIG. 8, the fingers or columns comprising the mass of pores material need not be "in" a compartment. Parts similar to those previously described bear the same reference numeral to which a distinguishing suffix "C" is appended. Thus, in the "hair brush" embodiment container 10C comprises a flat wall surface 26C from which fingers 40C emanate. There is, however, no confining sidewall. As with all the previous embodiments, the fingers' size and spacing is such as to ensure that the column of water supported by capillary attraction is between about 2 and about 60 mm. Although they are shown as being cylindrical, fingers 40C can also be rectangular in cross section or tapered cones as per the embodiment of FIG. 7. Their length "l", FIG. 8, depends on the volume of liquid to be contained within the mass of fingers.

Although container 10C is shown as being mounted on a "vertical" wall, in zero or microgravities, "vertical" is arbitrary and the mounting surface can be anywhere.

Figure 9:
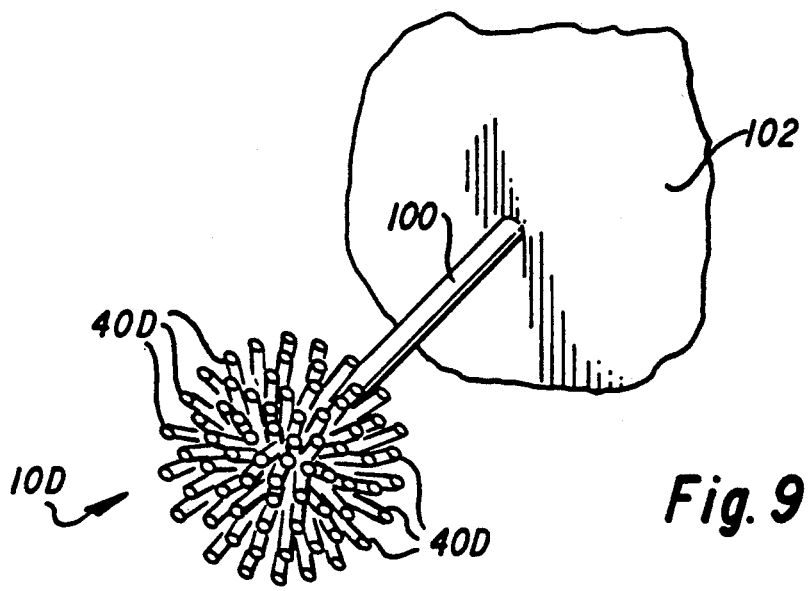
Figure 10:
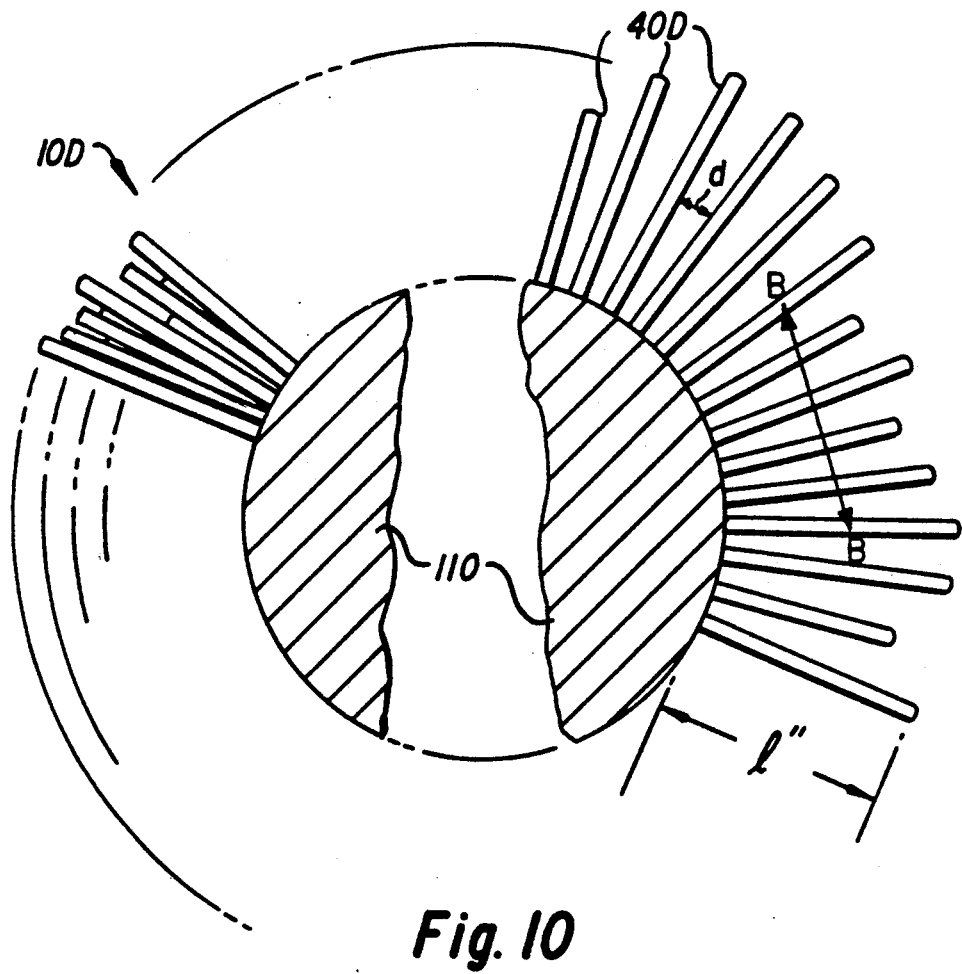
FIG. 10 is an enlarged fragmentary section view of the cluster shown in FIG. 9, only one "row" of fingers being illustrated on the right side to more clearly demonstrate their spacing.

Alternatively, the fingers of FIG. 6 need not be attached to any extensive surrounding surface, or even a flat surface, but can be joined together and emanate from a central core, FIGS. 9 and 10, which in turn has a support arm attached to a suitable wall support. Parts similar to those previously described bear the same reference numerals to which the suffix "D" is appended.

Thus, FIG. 9, in the "dandelion" embodiment container 40D comprises fingers 40D that project from a central core (hidden from view) attached to a support arm 100 attached to any surface 102. In such a case, the pore sizes will vary as a function of the distance the pore is measured from the core, so that care needs to be taken to size the fingers and their spacing to generally achieve the support of a water column of 2 to 60 mm through a significant portion of the volume. This is most easily achieved by having a relatively large diameter core 110, compared to the length "l" of the fingers 40D as is better shown in FIG. 10 instead of FIG. 9. The reason is that such a relationship will change the angle each finger occupies relative to its neighbors, a minimum amount, thus making the column height of about 2 to 60 mm more easily achieved. Thus, as shown on the right side of core 110, fingers 40D extend from surface 26D of the core at varying angles, but because the diameter of core 110 is so large, the spacing "d" between fingers 40D increases only slightly with increasing distance from surface 26D. The resulting capillary attraction can be easily controlled and the column height of supported liquid be readily achieved along line B—B.

FIG. 10 also illustrates that length "l" of fingers 40D can be varied as the fingers' location on surface 26D varies.

The removal of liquid by an aspirator, from container 10D, proceeds as in the previous embodiments. That is, the flexibility of fingers 40D readily allows the insertion of an aspirator into the site portion occupied by the liquid, a portion that is readily visible to the user.

After container 40D is used sufficiently, it can be disposed of with any residual body liquid, simply by detaching it from surface 102, and discarding it.

The invention has been described in detail with particular reference to preferred embodiments thereof, but it will be understood that variations and modifications can be effected within the spirit and scope of the invention.

What is claimed is:

1. In combination, a liquid aspirator and a container for body liquids to be aspirated by said aspirator, said container comprising:
a mass of compatible porous material that will absorb and be wetted by the body liquid of choice, and means for holding said mass of material, and any liquid contained therein, in a predetermined location, said mass of material comprising (a) fibers or fingers having a capillary attraction which will support a column of water that is between about 2 mm and about 60 mm in height, or (b) an open-cell foam having liquid attraction and liquid retention that is equivalent to that of said fibers.

2. A combination as defined in claim 1 wherein said mass comprises a fiber manufactured from cotton, glass, nylon, polyester coated with an acrylic or polyvinyl chloride, or cellulose acetate.

3. A combination as defined in claim 1 or 2, wherein said holding means comprise a cup in which said mass is retained.

4. A combination as defined in claim 1 or 2, wherein said mass is sufficiently releasable of the liquid during aspiration that, when tested using an aspirating pipette and any desired partial vacuum, enough liquid is drawn into the pipette so that no more than about 1 $\mu$l of air follows the liquid after aspiration due to residual vacuum created by liquid retention in said mass.

5. A combination as defined in claim 1, wherein said mass comprises a plurality of flexible columns projecting generally parallel to each other from a wall of said container.

6. A combination as defined in claim 1, wherein said mass of material comprises a urethane foam with a pore distribution of about 2 to 8 pores/cm.

7. A combination as defined in claim 1, wherein said mass of material comprises a melamine foam with a pore distribution of about 12 to 40 pores/cm.

8. A method of aspirating body liquids in an environment of reduced gravity, comprising
injecting the liquid into a site portion of a mass of wettable liquid-compatible porous material that will absorb the body liquid, said mass of material comprising (a) fibers or fingers having a capillary attraction which will support a column of water that is between about 2 mm and about 60 mm in height, or (b) an open-cell foam having liquid attraction and liquid retention that is equivalent to that of said fibers;
inserting the open end of an aspirator into said mass of porous material at said site portion in which the liquid resides,
and creating a sufficient partial vacuum in the aspirator to draw at least some of the liquid out of the mass of material.

9. A method as defined in claim 8, wherein the capillary attraction of said mass is such that, for said partial vacuum creation, no more than 1 $\mu$l of air follows the liquid aspiration due to residual vacuum created by said capillary attraction.

* * * * *